(12) United States Patent
Payandeh et al.

(10) Patent No.: US 6,997,866 B2
(45) Date of Patent: Feb. 14, 2006

(54) DEVICES FOR POSITIONING IMPLEMENTS ABOUT FIXED POINTS

(75) Inventors: Shahram Payandeh, Coquitlam (CA); Temei Li, Vancouver (CA); Hendrick Van Der Wal, Maple Ridge (CA)

(73) Assignee: Simon Fraser University, Burnaby (CA)

( * ) Notice: Subject to any disclaimer, the term of this patent is extended or adjusted under 35 U.S.C. 154(b) by 296 days.

(21) Appl. No.: 10/413,370

(22) Filed: Apr. 15, 2003

(65) Prior Publication Data

US 2004/0024387 A1 Feb. 5, 2004

Related U.S. Application Data

(60) Provisional application No. 60/372,195, filed on Apr. 15, 2002.

(51) Int. Cl.
*A61B 1/00* (2006.01)

(52) U.S. Cl. ...................................................... 600/102
(58) Field of Classification Search ................. 600/102, 600/227; 606/1, 130; 248/176.1, 186.1, 186.2, 248/317, 324
See application file for complete search history.

(56) References Cited

U.S. PATENT DOCUMENTS 6,361,488 B1 * 3/2002 Davison et al. ............. 600/102
6,569,084 B1 * 5/2003 Mizuno et al. ............. 600/102

* cited by examiner

*Primary Examiner*—Beverly M. Flanagan
(74) *Attorney, Agent, or Firm*—Oyen Wiggs Green & Mutala LLP

(57) ABSTRACT

A method and apparatus for a spherical parallel mechanism are disclosed. The invention involves a platform and at least three kinetic chains. The kinetic chains each comprise a link with one end pivotally coupled to the platform about a first axis and a second end pivotally coupled to an arm about a second axis. The arms in all of the kinetic chains share a common third axis. All of the first, second and third axes for all of the kinetic chains pass through a stationary point in space. Movement of the arms to selected angular positions about the common third axis adjusts an orientation and position of the platform about a spherical surface centered at the stationary point. The parallel mechanism has particular advantages for manipulating implements, such as cameras used in laparoscopic surgery, when the implements are mounted to the mobile platform.

45 Claims, 10 Drawing Sheets

DEVICES FOR POSITIONING IMPLEMENTS ABOUT FIXED POINTS

CROSS-REFERENCE TO RELATED APPLICATION

This application claims the benefit of the filing date of U.S. Application No. 60/372,195 filed 15 Apr. 2002, which is hereby incorporated by reference.

TECHNICAL FIELD

The invention relates to parallel mechanisms for holding and manipulating implements. The invention has particular application in holding implements for use in laparoscopic surgery.

BACKGROUND

Laparoscopic surgery is a type of surgery in which surgical instruments enter a subject's body through small cuts in the subject's skin, avoiding the relatively large incisions common in conventional surgery. During laparoscopic surgery, the surgeon observes the surgical field by way of a video camera, which is also inserted through a cut in the subject's skin. In a process known as insufflation, a gas, such as $CO_2$ may be introduced into a body cavity within which the surgery is being performed to provide room for the surgical instruments to operate.

Laparoscopic implements are conventionally manipulated directly by a person, typically a surgeon.

The inventors have identified a need for a support capable of holding and manipulating a laparascopic implement, such as a camera or other implement.

SUMMARY OF THE INVENTION

This invention provides a support capable of changing the orientation of an implement without imparting translational movement to a portion of the implement that coincides with a stationary point.

The apparatus according to a first embodiment of the invention comprises a platform and at least three links. Each of the links has a first end pivotally coupled to the platform and is rotatable relative to the platform about a corresponding first axis. The mechanism also comprises an arm corresponding to each of the links. Each of the arms is pivotally coupled to a second end of the corresponding link and is rotatable relative to the corresponding link about a corresponding second axis. All of the arms are rotatable about a common third axis, which is spaced apart from their respective second axes. All of the first, second and third axes extend through a stationary point in space. Movement of the arms to selected angular positions about the common third axis alters an orientation of the platform about the stationary point. The stationary point remains substantially stationary.

The apparatus may also comprise a rotary actuator coupled to each of the arms, which may be coupled to its corresponding arm by one of a plurality of shafts that are parallel to the third axis. The shafts may be concentric and a first one of the shafts may be received in a bore of a second one of the shafts, while a third one of the shafts is received within a bore of the first one of the shafts. The shafts may have a length in excess of 1, 2, 5, or 16 times a diameter of the platform and, in some embodiments, have lengths in the range of 1 and 10 times the diameter of the platform.

The links and arms may be curved. The radius of curvature for each of the arms may be different. The arm corresponding to the second one of the shafts may have a larger radius of curvature than that of the arm corresponding to the first one of the shafts. The arm corresponding to the third one of the shafts may have a shorter radius of curvature than that of the arm corresponding to the first one of the shafts. Similarly, the arm corresponding to the second one of the shafts may be longer than the arm corresponding to the first one of the shafts and the arm corresponding to the third one of the shafts may be shorter than the arm corresponding to the first one of the shafts.

The first end of each of the links may be coupled to the platform through a corresponding member that extends from the base of the platform along the corresponding first axis. Further, the first ends of the links may be pivotally coupled to the platform at various locations thereon. The various coupling locations may be equally spaced apart around the platform.

The movement of the arms to selected angular positions about the common third axis may also alter the position of the platform about the stationary point. The position and orientation of the platform may be adjusted over a spherical surface centered at the stationary point.

The apparatus may also comprise a base, which is spaced apart from the platform and is adapted to support the rotary actuators and the plurality of shafts. The base may be coupled to a support and may be adjustable relative to the support. The base may be space apart from the platform by a distance that ranges between 1 and 10 times the diameter of the platform.

The base may be (or may be affixed to) the platform of a similar secondary parallel mechanism. In this manner, a plurality of such devices may be "daisy chained" together to provide additional degrees of freedom.

The apparatus may comprise a joint, which is coupled to the arms and which allows the arms to rotate about the common third axis. The joint may be mounted on the platform of a similar secondary parallel mechanism to provide additional degrees of freedom.

The apparatus may include an implement affixed to the platform such that the active portion of the implement may be within operational range of the stationary point. That is, the implement may be able to perform its function (whatever that function may be) in a volume of space that includes the stationary point.

In some embodiments, the stationary point is spaced apart from the platform by a distance not exceeding 3 times a diameter of the platform. Alternatively, the stationary point may be located inside the volume of space occupied by the extremities of the platform.

Another aspect of the present invention provides a parallel mechanism, which comprises a platform, a base and at least three kinetic chains. The base may be spaced apart from the platform by a distance that ranges between 1 to 10 times the diameter of the platform. Each kinetic chain has a link with a first end rotationally coupled to the platform about a first axis and an arm rotationally coupled to the base about a second axis. The link and the arm in each kinetic chain are rotationally linked to one another about a third axis. All of the first, second and third axes for all of the kinetic chains extend through a stationary point in space. The angle subtended by any two of the second axes relative to their intersection with the stationary point may be less than $\pi/12$ radians. Movement of the arms to selected positions about their respective second axes adjusts the orientation of the platform about the stationary point.

Another aspect of the present invention is a method of orientating and positioning a platform about a stationary point in space. The method comprises providing at least three links. Each of the links has a first end pivotally coupled to the platform and is rotatable relative to the platform about a corresponding first axis. The method also comprises providing an arm corresponding to each link. Each of the arms is pivotally coupled to the corresponding link and is rotatable relative to the corresponding link about a corresponding second axis. All of the arms are rotatable about a common third axis, which is spaced apart from their respective second axes. All of the first, second and third axes extend through the stationary point. The method also comprises moving the arms to selected angular positions about the common third axis, so as to adjust a pose of the platform over an imaginary spherical surface centered at the stationary point.

Moving the arms to selected angular positions may comprise moving the links, moving the first axes and moving the second axes. Movement of all of the arms may occur simultaneously.

The method may comprise fixing an implement to the platform, such that an active portion of the implement is located within operational range of the stationary point. That is, the implement may be able to perform its function (whatever that function may be) in a volume of space that includes the stationary point.

Further aspects of the invention and features of specific embodiments of the invention are described below.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
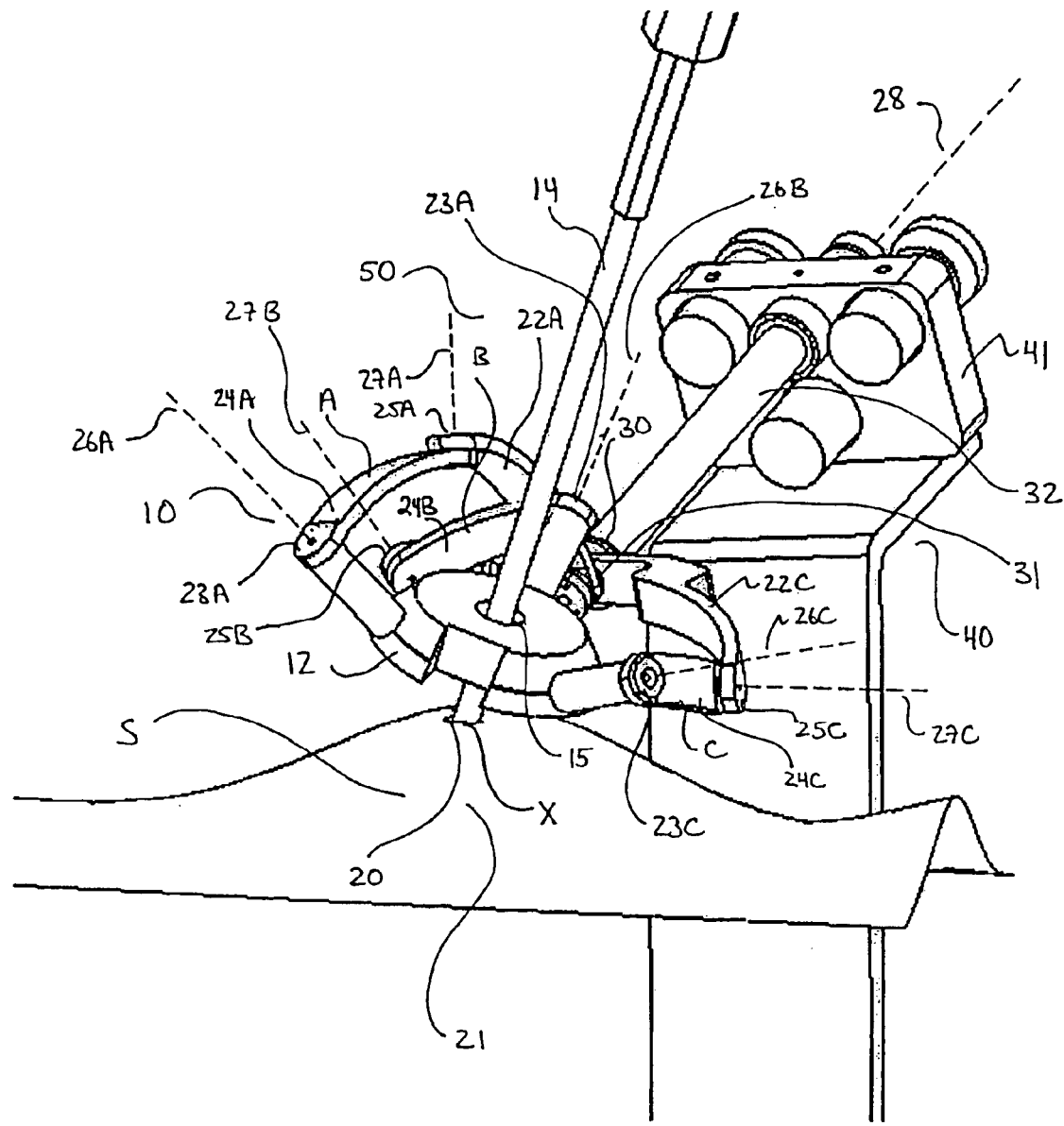
FIG. 1 is a schematic representation of an implement manipulating device according to one embodiment of the invention.

FIG. 1 illustrates an implement manipulating device 50 according to one embodiment of the invention. The implement manipulating device 50 of FIG. 1 comprises a parallel mechanism 10 and a support structure 40. Parallel mechanism 10 comprises a mobile platform 12, supported by kinetic chains A, B and C. Mobile platform 12 may be adapted in any of a wide range of ways to permit the mounting of an implement 14. In the illustrated embodiment, implement 14 passes through and slidably engages a bore 15 in mobile platform 12, such that implement 14 is coincident with the central symmetrical axis of mobile platform 12. A clamp (not shown) of any suitable construction may be provided to detachably fix implement 14 to mobile platform 12.

Although the construction of implement 14 and its function are not germane to this invention, in some applications implement 14 may be an elongated tool equipped with a camera on its active end for use in laparoscopic surgery. It should be understood that mobile platform 12 may be fitted with many other types of implements 14, having various shapes, sizes and features of their own. While implement manipulation device 50 has attributes that make it useful for laparoscopic surgery, those skilled in the art of robotics and parallel mechanisms will appreciate that the applications of implement manipulation device 50 are wide ranging in manufacturing, robotics and other fields and are not limited to laparoscopic surgery.

In this description, a number of words and phrases particular to the art of robotics are used to describe the invention. A "kinematic chain" is an assemblage of arms, links and joints. A "revolute joint" is a type of joint, which permits two members to rotate relative to one another. A "pose" is a configuration of an apparatus wherein a part has a certain position and orientation. Throughout this description and the accompanying claims, these words and phrases should be interpreted with the meanings set out above.

Figure 3:
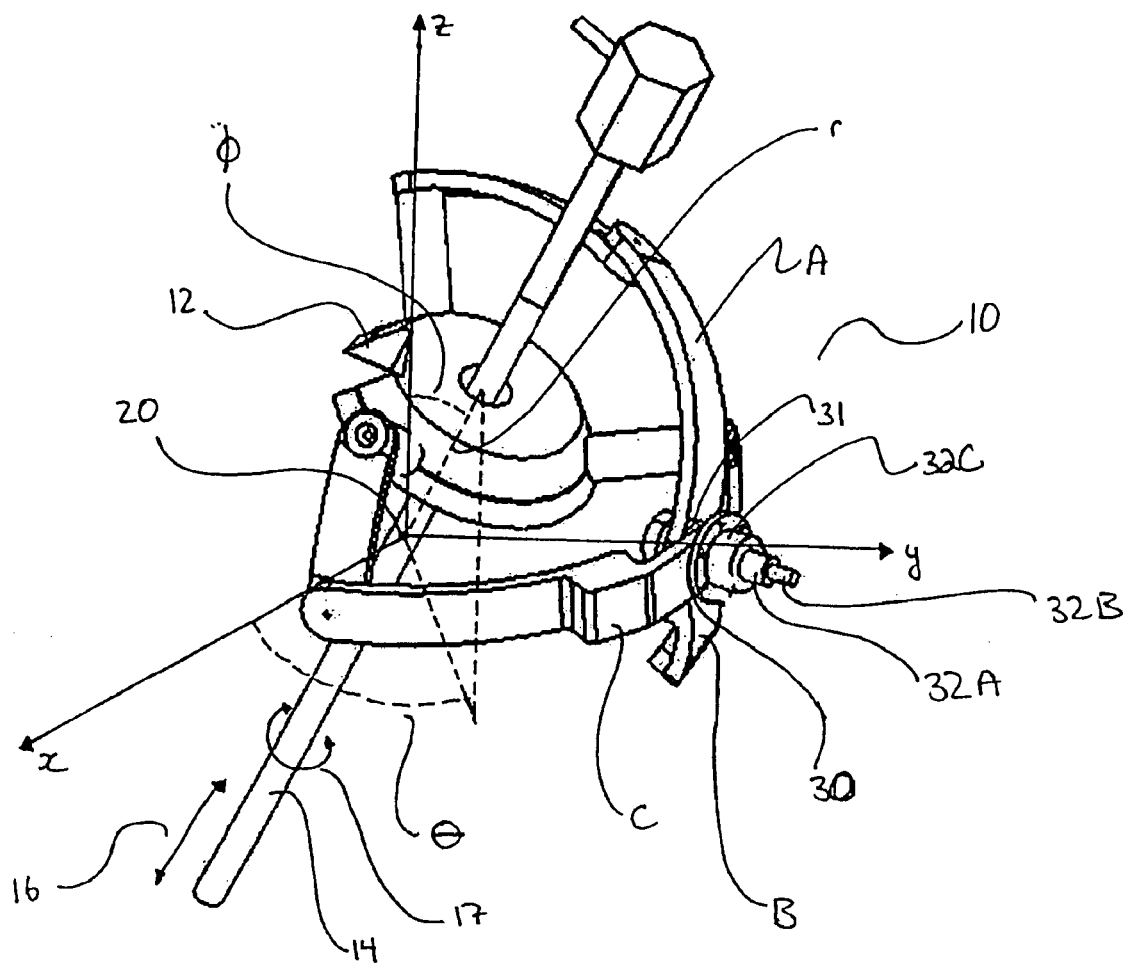
FIG. 3 depicts the parallel mechanism of FIG. 2 in a different orientation.
Figure 8:
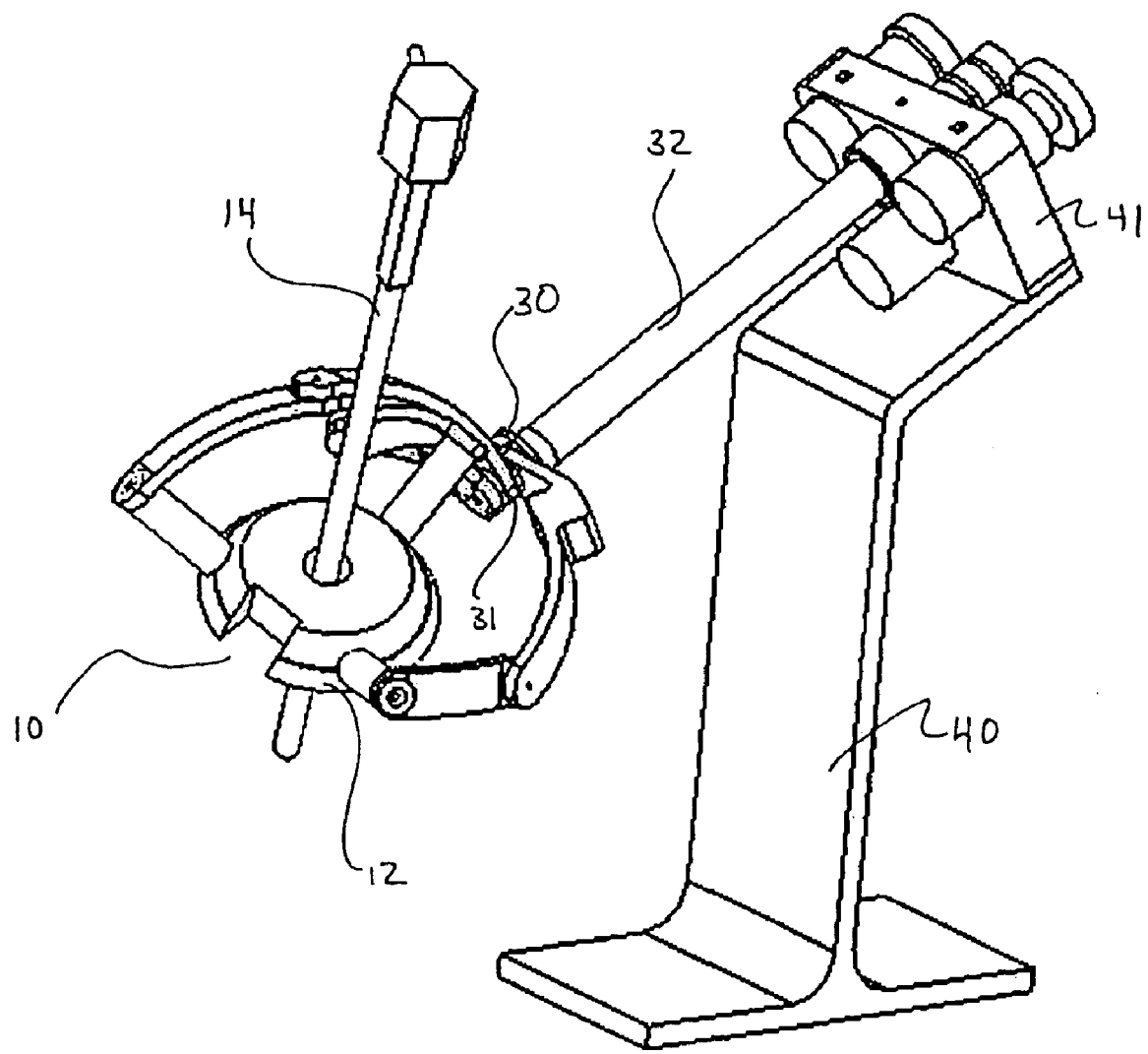
FIG. 8 is an embodiment of the implement manipulation device having a support structure suitable for use in laparoscopic surgery.
Figure 9:
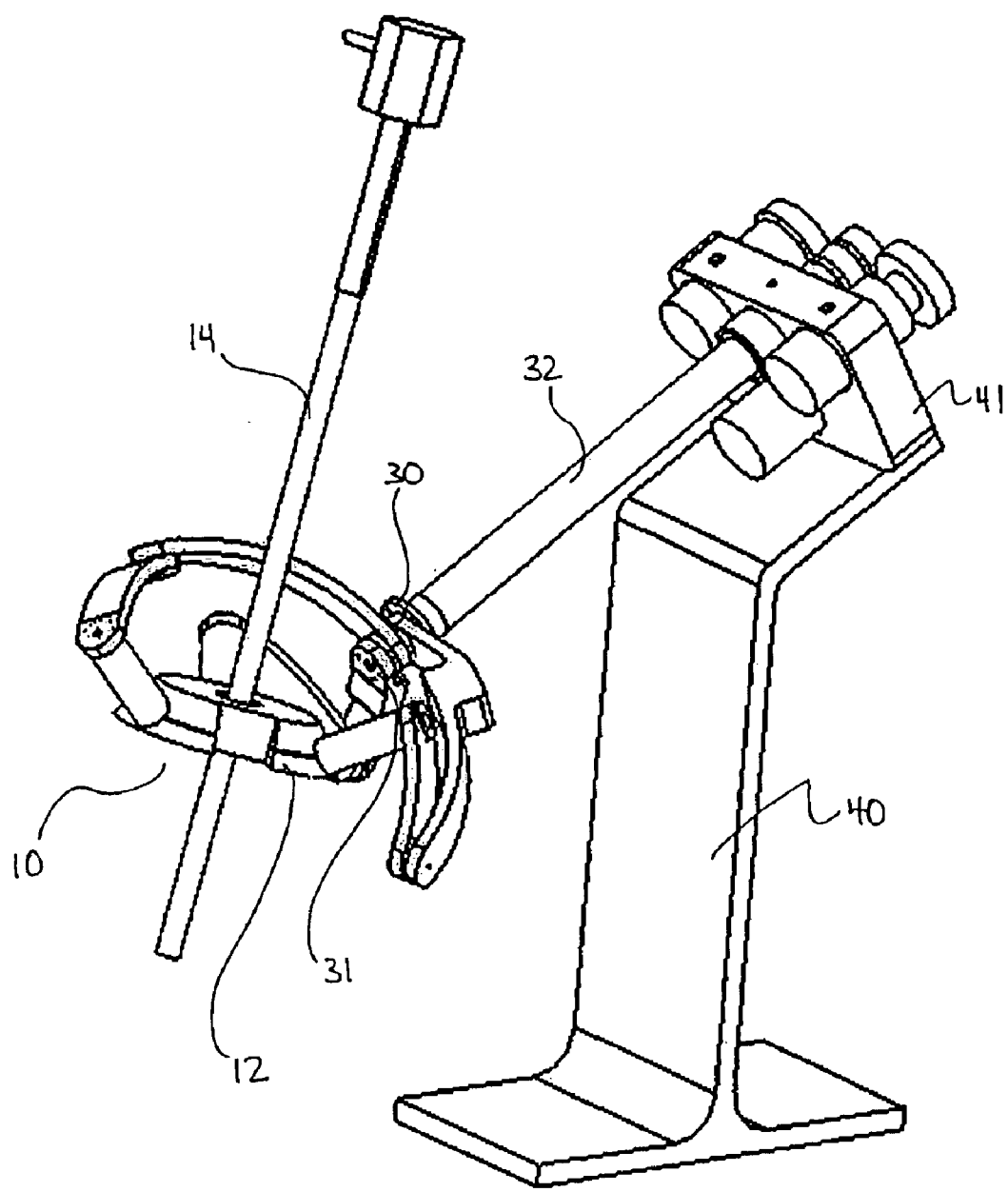
FIG. 9 shows the implement manipulation device of FIG. 8 in a different orientation.

Referring to FIGS. 1, 8 and 9, parallel mechanism 10 can move mobile platform 12 over an imaginary spherical surface (not shown) centred at a "stationary point" 20, which is in or adjacent to workspace 21. The active end of implement 14 may be selected to coincide roughly with stationary point 20. If such a selection is made, the spherical movement of platform 12 causes the active end of implement 14 to remain essentially stationary, while varying the orientation of implement 14 about stationary point 20. The orientation of platform 12 and implement 14 about stationary point 20 may be expressed, for example, by the angles θ and φ of a spherical coordinate space as shown in FIG. 3. Mechanisms that operate in this manner are referred to generally as "spherical parallel mechanisms".

In a preferred embodiment related to laparoscopic surgery, implement 14 comprises a camera and the workspace 21 for the spherical parallel mechanism 10 is a volume that includes the surgical region of interest inside the body of a subject S (see FIG. 1). In this embodiment, implement 14 enters the body of subject S through a small cut X. The stationary point 20 can be made to coincide generally with cut X. For this reason, the point at which implement 14 passes through cut X may remain essentially stationary during the movement of mobile platform 12(in the permitted directions θ and φ). The movement of mobile platform 12 adjusts the orientation of implement 14 about stationary point 20. The field of view of a camera in implement 14 may be adjusted over the entire surgical field spanned by the angles θ and φ.

In a more general application, it will be appreciated that parallel mechanism 10 of the present invention manipulates mobile platform 12 between poses (i.e. positions and orientations) on a spherical surface surrounding a stationary point 20. Implement 14 may be mounted on mobile platform 12, such that the orientation of implement 14 may be similarly manipulated about stationary point 20. The radius of the imaginary spherical surface over which mobile platform 12 may be manipulated is determined by the geometries of the components of parallel mechanism 10, including links 24, arms 22 and platform 12. These dimensions may be selected to minimize the interference of platform 12 and implement 14 in the desired workspace 21.

In general, implement 14 can be any tool and may itself be manipulable independent of kinetic chains A, B and C. For example, depending on the application, implement 14 may be moved longitudinally in an "r" direction as indicated by arrow 16 (compare FIGS. 2 and 3) or may be rotated about its longitudinal axis (which extends in the r direction) as indicated by arrow 17. A suitable linear actuator 37 (see FIG. 10), such as a rotatable lead screw, may be mounted on mobile platform 12 or within the body of implement 14. The linear actuator may be operated to adjust the position of implement 14 in the r direction of arrow 16. In general, any suitable actuator capable of providing translational movement may be used for this purpose. Similarly, any rotational actuator may be used to rotate the implement 14 about the r axis in the direction of arrow 17. Implement 14 may also be equipped with actuators (not shown) that allow it to be manually or automatically operated.

Figure 2:
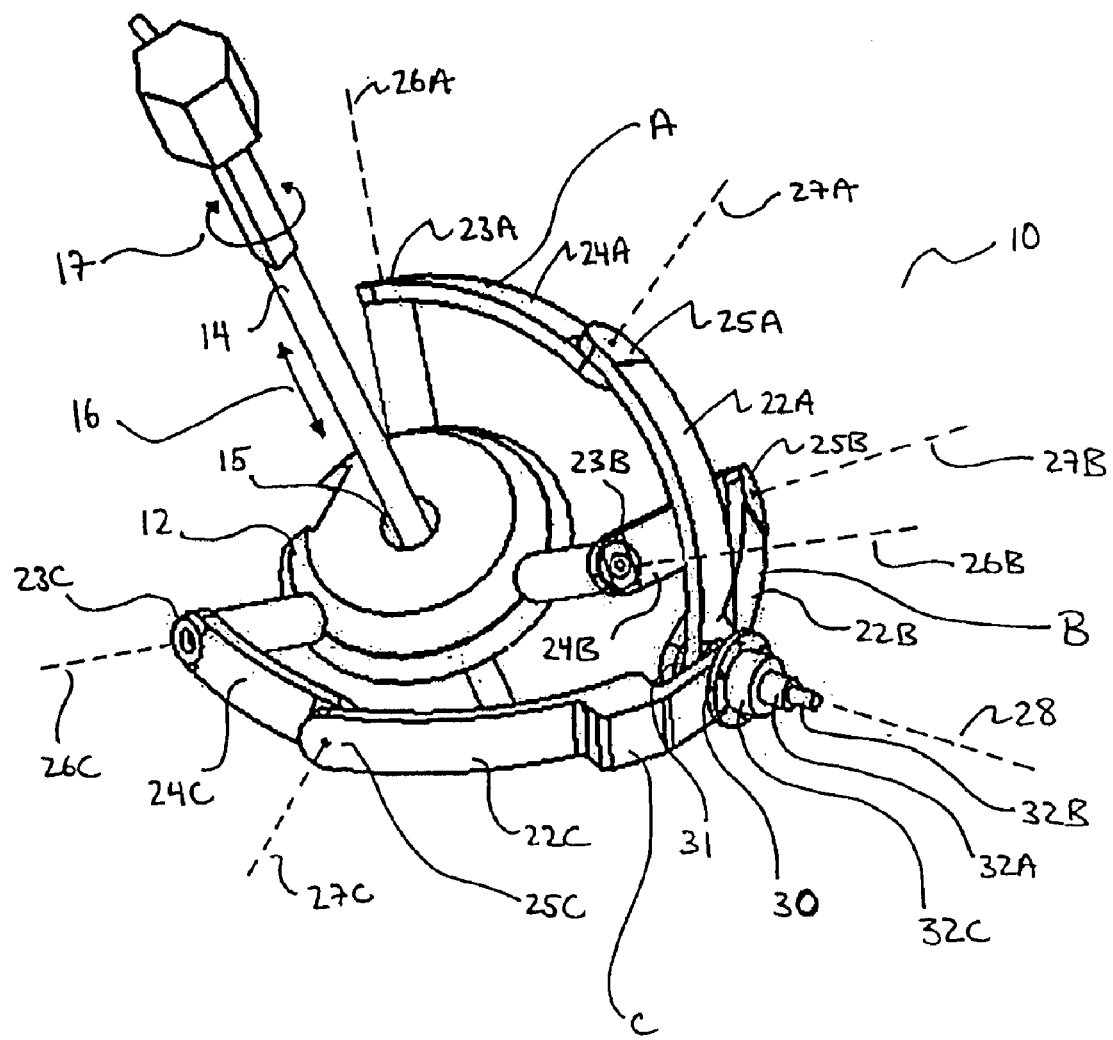
FIG. 2 is an isometric view of the parallel mechanism from the implement manipulating device of FIG. 1.

FIGS. 1, 2 and 3 illustrate a preferred embodiment of spherical parallel mechanism 10 in which mobile platform 12 is supported by three kinematic chains A, B and C. Kinematic chains A, B and C comprise three arms 22A, 22B and 22C (referred to collectively as arms 22) and three links 24A, 24B and 24C (referred to collectively as links 24). Each of links 24 has a first end pivotally coupled to mobile platform 12 at one of revolute joints 23A, 23B and 23C (referred to collectively as joints 23). Joints 23 permit rotation about a corresponding one of axes 26A, 26B, and 26C (referred to collectively as axes 26). Each of axes 26 extends through a stationary point 20. Each of links 24 has a second end coupled to the corresponding arm 22 at one of revolute joints 25A, 25B and 25C (referred to collectively as joints 25). Joints 25 permit rotation about a corresponding one of axes 27A, 27B, and 27C (referred to collectively as axes 27). Each of axes 27 also extends through stationary point 20. Finally, each of arms 22 attaches to support structure 40 via composite revolute joint 31 and shaft assembly 30, such that arms 22 may be controllably rotated about a common axis 28. Common axis 28 of composite revolute joint 31 also extends through stationary point 20.

The pose of mobile platform 12 and orientation of implement 14 about stationary point 20 may be altered by simultaneously controlling the three kinematic chains A, B and C. Control of the three kinematic chains A, B and C is effected by manipulating composite joint 31 to rotate arms 22 to selected angular positions about common axis 28. It will be appreciated that movement of arms 22 at composite joint 31 causes corresponding movement of links 24 at joints 23 and 25.

In the illustrated embodiment, parallel mechanism 10 is supported at a distal end of a shaft assembly 30 comprising three concentric shafts 32. Each of arms 22 is coupled to a distal end of a corresponding one of shafts 32 via composite revolute joint 31. In FIGS. 2 and 3, parts of shaft assembly 30 are cut away to depict its functional elements. A first shaft 32A is connected to first arm 22A. A second shaft 32B extends through a bore of shaft 33A and connects to second arm 22B. Shafts 32A and 32B both pass through a bore in a third shaft 32C. Third shaft 32C is connected to third arm 22C. Depending on the application, shaft assembly 30 may have a significant length. Shaft assembly 30 may have a length which equals or exceeds 1, 2, 5 or 10 times a diameter of the platform 12, for example. In some embodiments, shaft assembly 30 has a length in the range of 1 to 10 times a diameter of platform 12.

Figure 5:
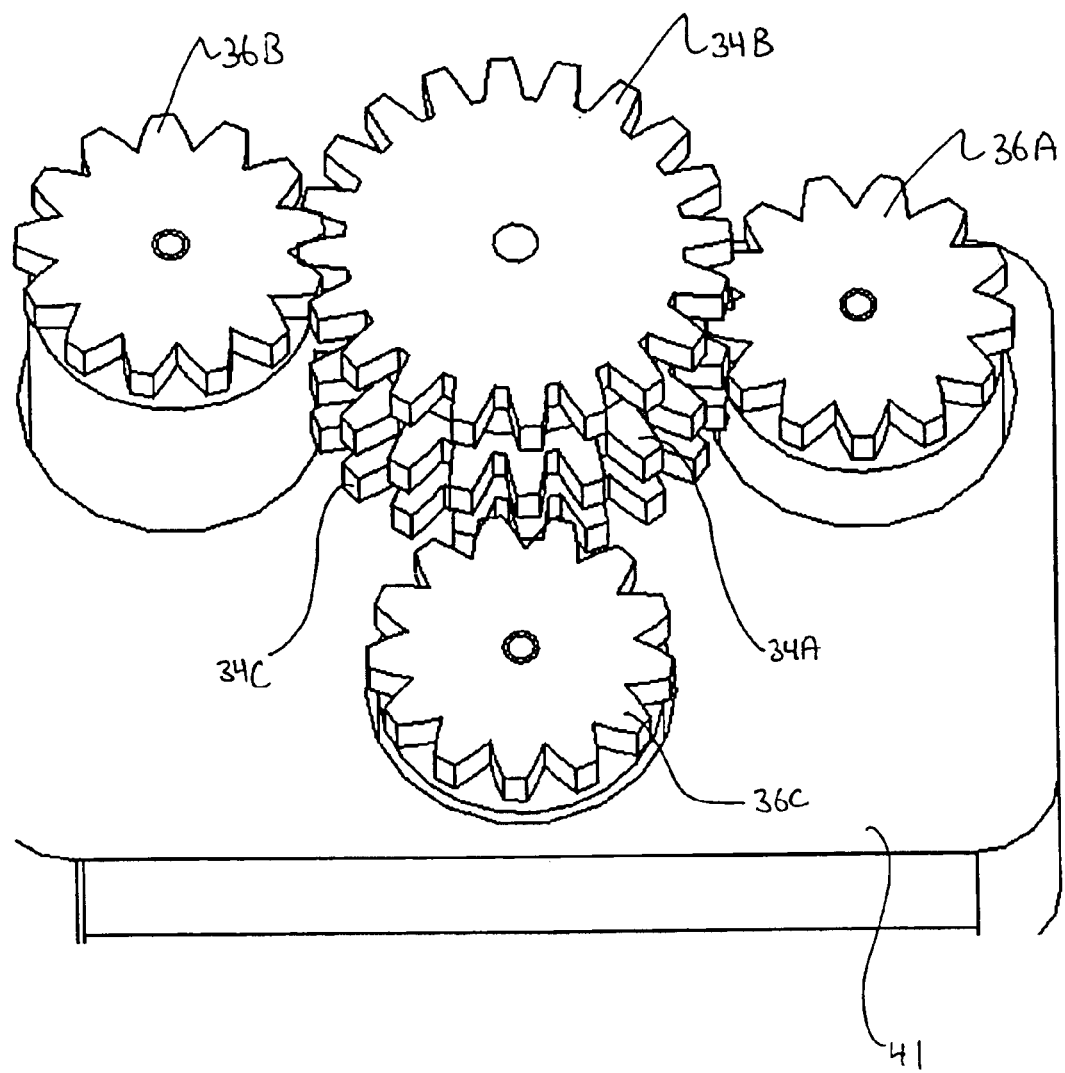
FIG. 5 depicts several gear linkages, which comprise one embodiment for driving the parallel mechanism.
Figure 6:
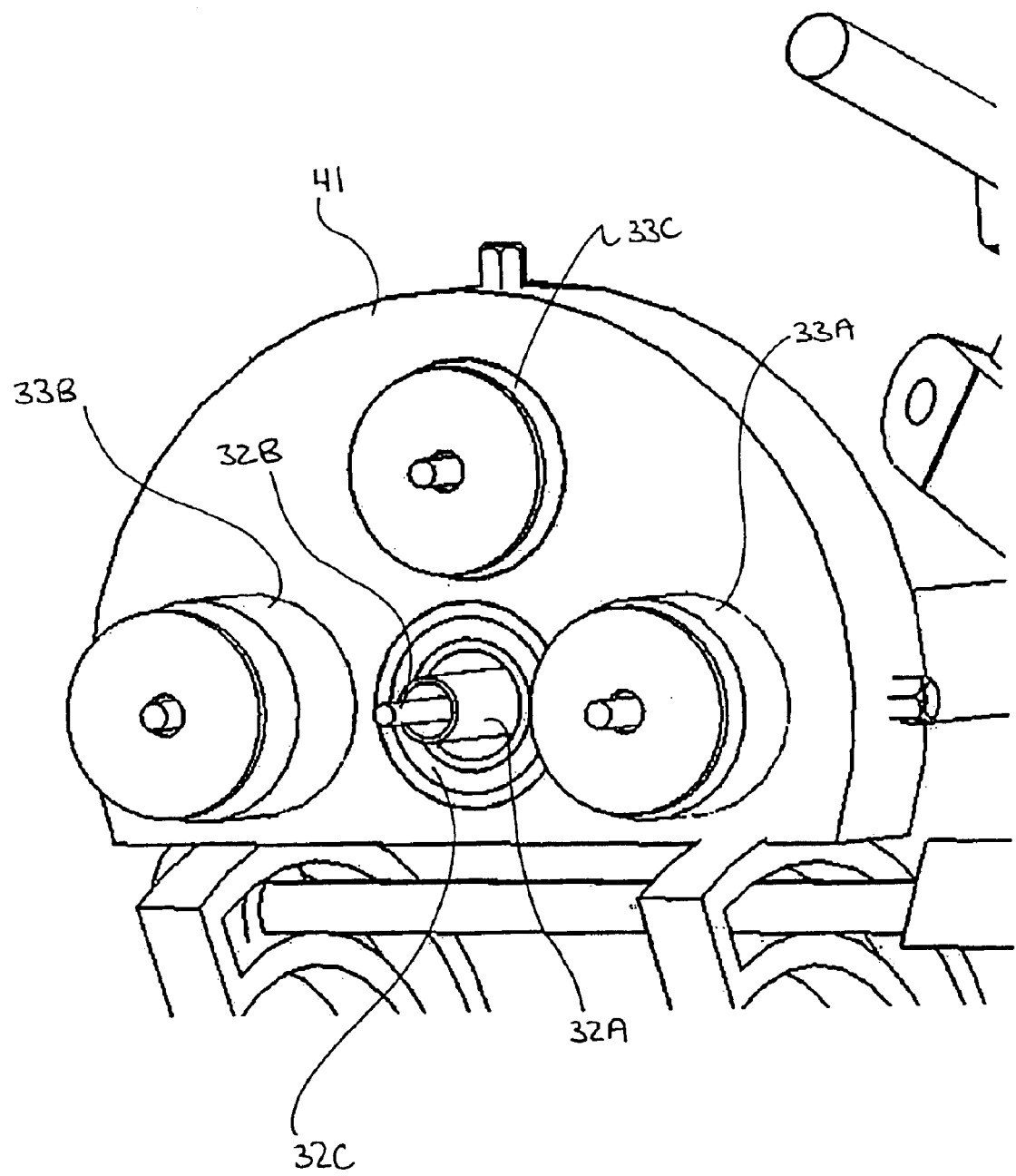
FIG. 6 shows three motor shafts and a composite drive shaft for one embodiment of the parallel mechanism.
Figure 7:
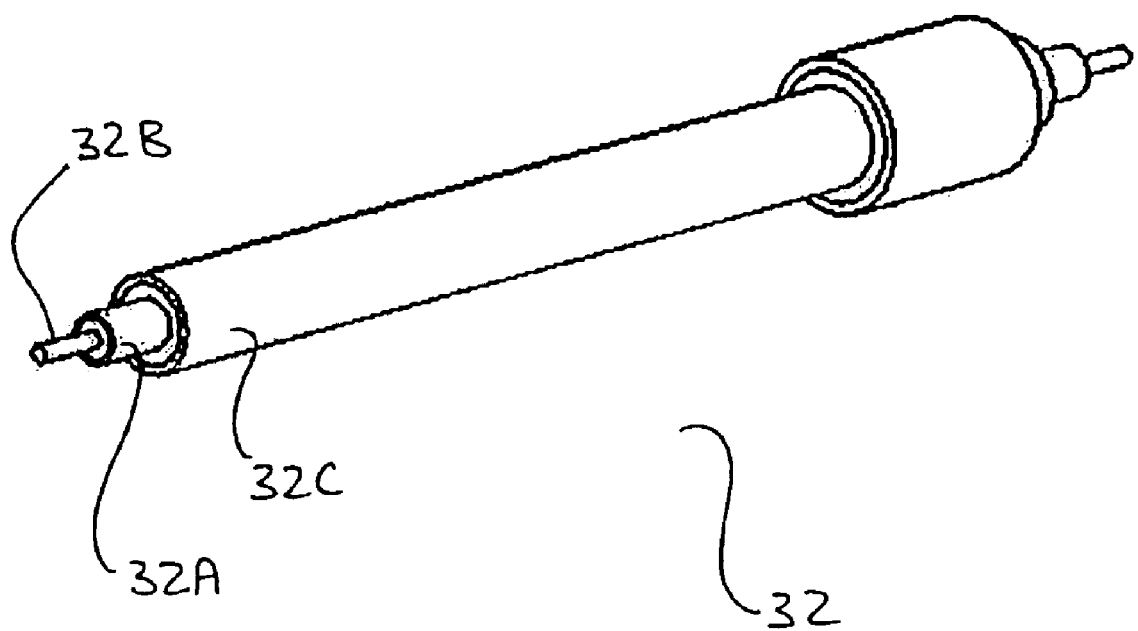
FIG. 7 depicts the concentric composite drive shaft for one embodiment of the implement manipulation device.

The angle of rotation of each of concentric shafts 32 is controlled by a corresponding rotary actuator, such as a motor 33, which is mounted on base 41 of support structure 40. Motors 33 may comprise, for example, stepper motors or AC or DC servo motors. FIG. 5 depicts a schematic diagram of an embodiment where three gears 34A, 34B and 34C (one corresponding to each shaft 32A, 32B and 32C) are mounted on base 41 at the proximal ends of concentric shafts 32. Each of gears 34 are independently driven by a pinion gear 36 coupled to the shaft of a corresponding one of motors 33. Rotation of motors 33 orients mobile platform 12 as desired through the cooperation of gears 36 and 34, concentric shafts 32 and kinematic chains A, B and C. It will be appreciated by those skilled in the art that there are many possible mechanical couplings, which may be used to couple motors 33 (mounted on base 41) to concentric shafts 32. For example, shafts 32 may be actuated by chain or pulley mechanisms. The invention should be understood to incorporate any suitable means for independently coupling motors 33 to concentric shafts 32.

The shaft angles of motors 33 are controlled by an electronic control system (not shown). Sensors (not shown), such as optical encoders, may be used to track the shaft angle of the motors 33. It will be appreciated to those skilled in the art of control systems that a kinematic model may be generated to describe the pose of platform 12 for a given set of shaft angles of motors 33. Using inputs from the shaft angle sensors in combination with such a kinematic model, software running in a controller (not shown) controls the pose of mobile platform 12 using well known control algorithms. Using such software, a user may input the desired pose of platform 12 at a remote location and the software will cause the controller to effect the desired orientational change by moving platform 12 through a desired set of intermediate poses.

Base 41 and motors 33 may be a significant distance from mobile platform 12 as shown in FIGS. 8 and 9. Depending on the application, the concentric shafts may have lengths equal to or exceeding 1, 2, 5 or 10 times a diameter of the platform 12, for example. In some embodiments, the concentric shafts may have lengths in the range of 1 to 10 times a diameter of platform 12. It will be appreciated that if shafts 32 are long enough, then base 41 and motors 33 are located well clear of the workspace 21. In this manner, the parallel mechanism 10, which is located adjacent to the workspace 21, can be relatively compact and much of the bulk (i.e. motors 33) can be spaced apart from workspace 21 on base 41. In addition to spacing base 41 and motors 33 from workspace 21, concentric shafts 32 (with their common rotational axis 28) represent a relatively narrow implementation, which contributes to the compactness and versatility of implement manipulation device 50. These aspects of the preferred embodiments provide particular advantages for laparoscopic surgery, because surgeons must occupy much of the area surrounding workspace 21 in order to perform medical procedures in workspace 21. In general, these aspects of the preferred embodiments provide advantages, because they minimize the volume adjacent to workspace 21 that is occupied by parallel mechanism 10, base 41, motors 33 and support structure 40.

FIGS. 8 and 9 illustrate an embodiment of the same implement manipulating device 50 with parallel mechanism 10 adjusted to place mobile platform 12 in two different poses. Parallel mechanism can be adjusted from the configuration of FIG. 8 to the configuration of FIG. 9 by using motors 33 to selectively rotate the three concentric shafts 32. Movement between the orientation of FIG. 8 and FIG. 9 involves the movement of mobile platform 12 over a spherical surface and can be done without imparting any significant translation to stationary point 20. In general, concentric shafts 32 are rotated simultaneously by motors 33 to change the pose of mobile platform 12. The relative rates and directions of rotation of shafts 32 that will cause mobile platform 12 to move from one pose to another through a particular continuum of intermediate poses are determined by the dimensions and geometry of parallel mechanism 10 and in particular, the geometries of the kinematic chains A, B and C. The electronic control software discussed above is configured to take these factors into account.

In the illustrated embodiment, arms 22 are curved (see FIG. 2). In this embodiment, each arm 22 follows an arc centered on the stationary point each of arms 22 has different physical characteristics, such as geometry, radius of curvature and/or length, so that arms 22 do not interfere with one another or with links 24 as they rotate at joints 27 and 31. Similarly, links 24 may have different physical characteristics, so as to engage effectively with their respective arms 22 at joints 27 and to ensure that they do not interfere with one another or with arms 22

Figure 10:
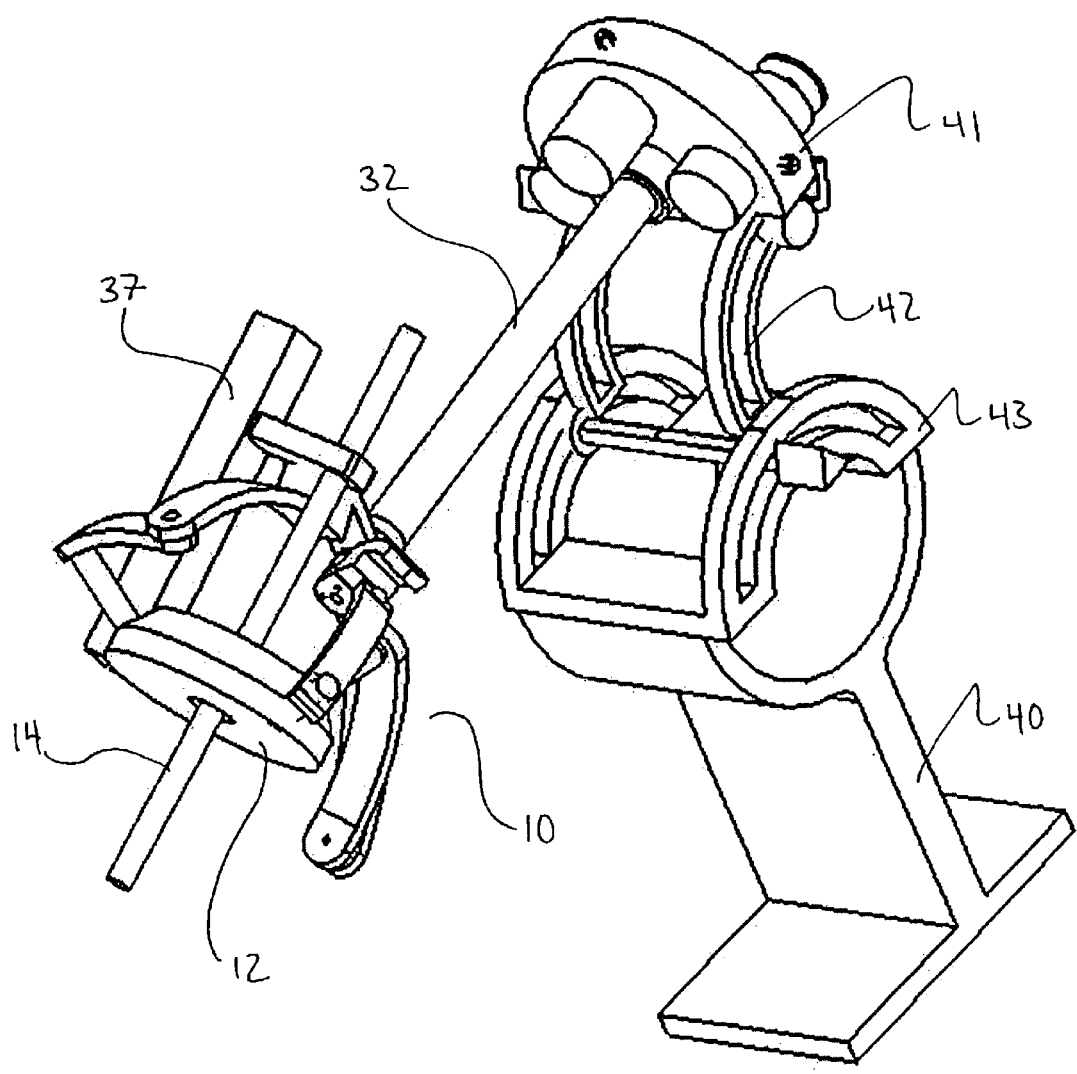
FIG. 10 depicts an alternative embodiment of the implement manipulation device, where the support structure itself is adjustable to provide the device with even greater range.

Manipulation device 50 may be mounted on a support structure 40, by way of a coupling which itself is manipulable. An example of such an embodiment is depicted in FIG. 10, which shows a parallel mechanism 10 similar to those discussed above. Base 41 is mounted on bracket 42, which is capable of moving at a hinge joint 43. Hinge joint 43 may be actuated manually or by a motor (not shown). Movement of hinge joint 43 changes the position and orientation of parallel mechanism 10 and the position of stationary point 20. Accordingly, the articulation of support structure 40 at hinge 43 may be used to position stationary point 20 at a desired location relative to workspace 21.

In another alternative embodiment, the implement manipulation device described herein has multiple "cascaded" parallel mechanisms 10. For example, base 41 of the embodiment depicted in FIGS. 8 and 9 may be attached to (or replaced by) the mobile platform of another parallel mechanism. Alternatively, implement 14 of the embodiment depicted in FIGS. 8 and 9 may itself comprise a parallel mechanism. In general, any embodiment of a spherical parallel mechanism 10 according to this invention may be cascaded with any other type of parallel mechanism, including both parallel mechanisms described herein and other types of parallel mechanisms. Such embodiments incorporating two parallel mechanisms provide a robotic instrument having six degrees of freedom. Having a second parallel mechanism also increases the flexibility with respect to locating stationary point 20 for applications in a variety of workplaces. Depending on the geometry of the implementation, such cascaded embodiments can offer three translational degrees of freedom and three rotational degrees of freedom about stationary point 20. The invention should be understood to incorporate a plurality of parallel mechanisms that are "daisy chained" together in this manner.

It should be appreciated that the above description relates to an ideal model. In practice, particular applications have an acceptable margin of deviations, which may permit some departure from the ideal behavior described above. For example, in many applications, it is not necessary for stationary point 20 to remain absolutely fixed as the orientation of parallel mechanism 10 changes. In an embodiment related to laparoscopic surgery, the skin of the subject is somewhat elastic. Consequently, movement of stationary point 20 up to 7 mm in any direction may be acceptable. Stationary point 20 may be said to be "essentially stationary" as long as its movement is less than the margin of deviation required for a particular application.

Similarly, axes 26, 27 and 28 are all described as "extending through" stationary point 20. However, due to mechanical inaccuracies or movement of stationary point 20, axes 26, 27 and 28 may not extend through stationary point 20 with mathematical precision. It is sufficient if axes 26, 27 and 28 extend through a stationary volume of space and that volume is sufficiently small that the implement manipulation device 50 continues to work within the applicable margin of deviation.

As will be apparent to those skilled in the art in the light of the foregoing disclosure, many alterations and modifications are possible in the practice of this invention without departing from the spirit or scope thereof. For example, arms 22 are described as being rotatable about a common axis 28 through composite joint 31 and concentric shafts 32. This configuration separates the base 41 and the motors 33 from the moving aspects of the parallel mechanism 10, which provides more space for the parallel mechanism 10 to move and more space for humans or other devices to work alongside the parallel mechanism 10. It would be possible to provide an implement manipulation device according to the present invention, wherein arms 22 are rotatable about three different axes 28A, 28B and 28C. Such an embodiment (not shown) may include a base 41, which comprises three different shafts 32A, 32B and 32C independently coupled to their respective arms 22. Either embodiment could function provided that the base 41 is located a suitable distance from the moving aspects of the parallel mechanism 10 and axes 28A, 28B and 28C are oriented so that they do not take up an inordinate amount of space. For example, an embodiment where the base 41 is separated from platform 12 by a distance in the range of about 1 to 10 times the diameter of the platform and the angle between any two of the axes 28A, 28B and 28C relative to their intersection at the stationary point is less than $\pi/12$ radians would still provide the necessary space for the parallel mechanism 10 to move and space to work alongside the parallel mechanism 10.

Figure 4:
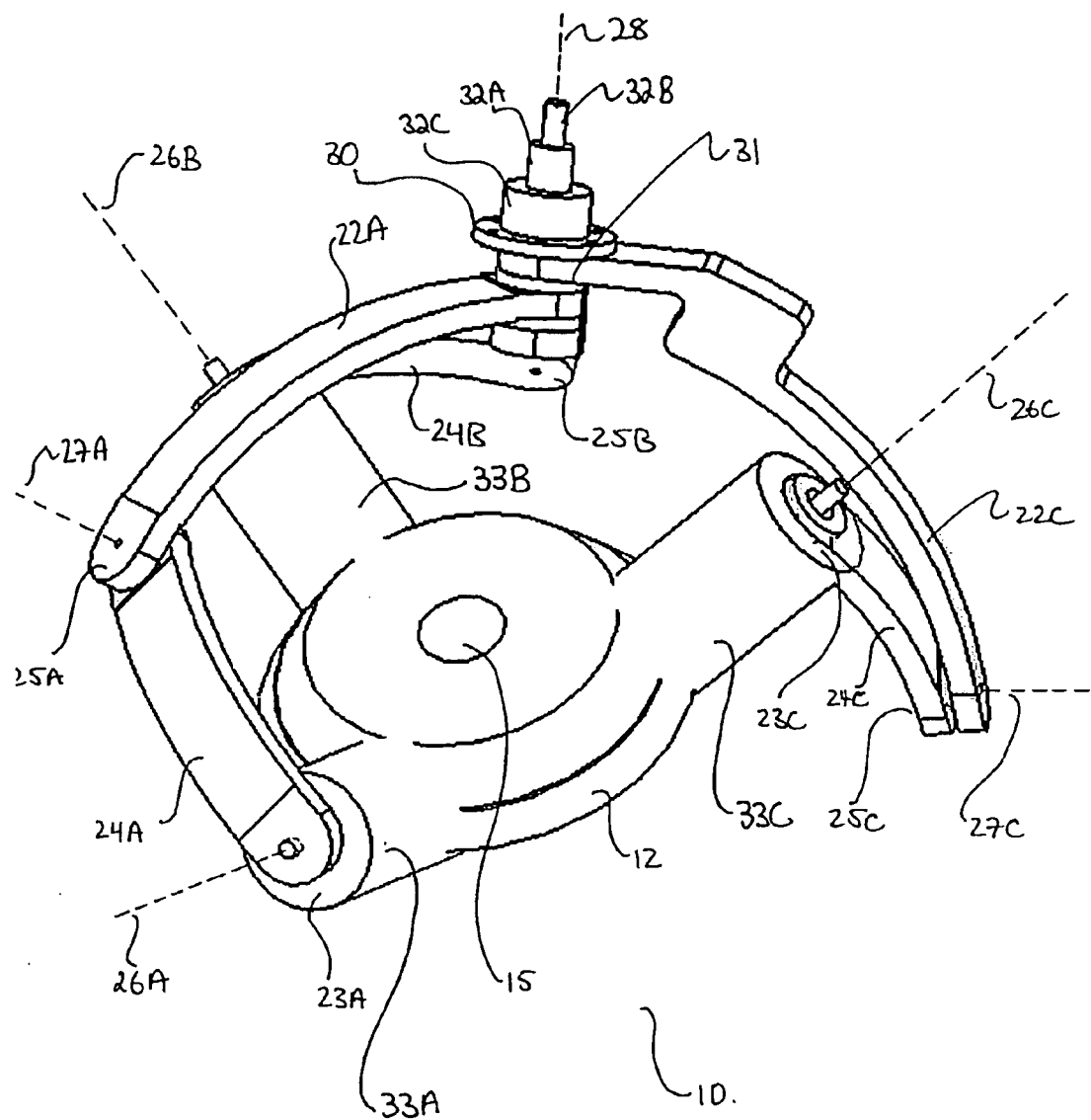
FIG. 4 is close up view of parallel mechanism according to one embodiment of the present invention.

Another example of an alternative embodiment is depicted in FIG. 4, where rotary actuators 33 are mounted at spaced apart locations on platform 12. In such an embodiment, kinetic chains A, B and C are driven by the shafts of their respective rotary actuators 33 at revolute joints 23, which rotate about their axes 26. Control of kinetic chains A, B and C may be determined by controlling the shaft angle of revolute joints 23 and composite revolute joint 31 may comprise a passive joint. With such an embodiment, it may also be possible to mount platform 12 on a stationary mount (not shown) and, though the actuation of revolute joints 23 and kinematic chains A, B and C, cause the position and orientation of composite revolute joint 31 to move over the surface of a sphere.

Additionally, while the devices described herein have had a mobile platform supported from three arms, a device according to the invention could have a different number of arms.

In a different alternative embodiment, platform 12 may be used as an "input device", where a user manipulates the position and or orientation of platform 12. Sensors coupled to the various pivotal joints (not shown) may be used to detect the motion of their corresponding joints and generate a set of corresponding electronic signals. In this manner, the invention may be used like a "joystick" input device for various applications.

Accordingly, the scope of the invention is to be construed in accordance with the substance defined by the following claims.

What is claimed is:

1. An apparatus for a parallel mechanism, the apparatus comprising:
    a platform;
    at least three links, each link having a first end pivotally coupled to the platform about a corresponding first axis; and
    an arm corresponding to each of the links, each arm pivotally coupled to a second end of the corresponding link about a corresponding second axis;
        all of the arms pivotable about a common third axis spaced apart from their corresponding second axes;
        all of the first axes, second axes and third axis extending through a stationary point;
    wherein an orientation of the platform is adjustable relative to the stationary point by moving the arms to selected angular positions about the third axis, without causing significant translation of the stationary point.

2. The apparatus of claim 1, comprising a rotary actuator corresponding to each of the arms, each rotary actuator coupled to the corresponding arm by a corresponding one of a plurality of shafts extending parallel to the third axis.

3. The apparatus of claim 2, wherein each of the plurality of shafts is concentric and a first one of the shafts is received within a bore of a second one of the shafts, while a third one of the shafts is received within a bore of the first one of the shafts.

4. The apparatus of claim 3, wherein the links are curved.

5. The apparatus of claim 4, wherein the arms are curved.

6. The apparatus of claim 5, wherein the arm corresponding to the second one of the shafts has a larger radius of curvature than the arm corresponding to the first one of the shafts and the arm corresponding to the third one of the shafts has a smaller radius of curvature than the arm corresponding to the first one of the shafts.

7. The apparatus of claim 3, wherein the arm corresponding to the second one of the shafts is longer than the arm corresponding to the first one of the shafts and the arm corresponding to the third one of the shafts is shorter than the arm corresponding to the first one of the shafts.

8. The apparatus of claim 1, wherein the first end of each of the links is pivotally coupled to the platform at an end of a corresponding member projecting from a base of the platform and extending along the corresponding first axis.

9. The apparatus of claim 8, wherein the members are located at locations equally spaced apart around a perimeter of the platform.

10. The apparatus of claim 1, wherein a position of the platform is adjustable relative to the stationary point by moving the arms to selected angular positions about the third axis, without causing significant translation of the stationary point.

11. The apparatus of claim 10, wherein the position and orientation of the platform are adjustable over at least a portion of an imaginary spherical surface centered at the stationary point.

12. The apparatus of claim 11, wherein a surface of the platform is oriented tangentially to the spherical surface during adjustment of the position and orientation of the platform.

13. The apparatus of claim 2, comprising a base, which is spaced apart from the platform and adapted to support the rotary actuators and the plurality of shafts.

14. The apparatus of claim 13, wherein the base is moveably coupled to a support.

15. The apparatus of claim 13, wherein the base is affixed to a secondary platform of a secondary parallel mechanism, the secondary parallel mechanism comprising:
    the secondary platform;
    at least three secondary links, each secondary link having a first end pivotally coupled to the secondary platform about a corresponding fourth axis; and
    a secondary arm corresponding to each of the secondary links, each secondary arm pivotally coupled to a second end of the corresponding secondary link about a corresponding fifth axis; and
        all of the secondary arms pivotable about a common sixth axis spaced apart from their corresponding fifth axes;
        all of the fourth axes, fifth axes and sixth axis extending through a secondary stationary point;
    wherein an orientation of the secondary platform and the base are adjustable relative to the secondary stationary point by moving the secondary arms to selected angular positions about the sixth axis, without causing significant translation of the secondary stationary point.

16. An apparatus according to claim 15, wherein the base is the secondary platform.

17. An apparatus according to claim 1, comprising a joint coupled to each of the arms at a location spaced apart from their respective second axes, the joint facilitating pivotal movement of the arms about the third axis.

18. An apparatus according to claim 17, wherein the joint is mounted on a secondary platform of a secondary parallel mechanism, the secondary parallel mechanism comprising:
    the secondary platform;
    at least three secondary links, each secondary link having a first end pivotally coupled to the secondary platform about a corresponding fourth axis; and
    a secondary arm corresponding to each of the secondary links, each secondary arm pivotally coupled to a second end of the corresponding secondary link about a corresponding fifth axis;
        all of the secondary arms pivotable about a common sixth axis spaced apart from their corresponding fifth axes;
        all of the fourth axes, fifth axes and sixth axis extending through a secondary stationary point;
    wherein an orientation of the secondary platform is adjustable relative to the secondary stationary point by moving the secondary arms to selected angular positions about the sixth axis, without causing significant translation of the secondary stationary point.

19. The apparatus of claim 1, comprising an implement affixed to the platform, the implement having an active portion located within operational range of the stationary point.

20. The apparatus of claim 19, wherein an orientation of the implement is adjustable relative to the stationary point by moving the arms to selected angular positions about the third axis, without causing significant translation of the active portion of the implement relative to the stationary point.

21. The apparatus of claim 20, wherein a position of the implement is adjustable relative to the stationary point by moving the arms to selected angular positions about the third axis, without causing significant translation of the active portion of the implement relative to the stationary point.

22. The apparatus of claim 21, wherein the position and orientation of the active portion of the implement are adjustable over at least a portion of an imagingary spherical surface centered at the stationary point.

23. The apparatus of claim 1, comprising an implement moveably mounted to the platform, the implement having an active portion positionable within an operational range of the stationary point.

24. The apparatus of claim 23, wherein the implement is moveable along an implement axis which extends from the stationary point along a radius of the spherical surface.

25. The apparatus of claim 24, wherein the implement is pivotable about the implement axis.

26. The apparatus of claim 25, wherein the platform is penetrated by a bore and the implement projects through and slidably engages the bore.

27. The apparatus of claim 26, wherein the bore is located in a symmetrical center of the platform.

28. The apparatus of claim 24 comprising an actuator for moving the implement along the implement axis, the actuator mounted to at least one of: the implement and the platform.

29. The apparatus of claim 25 comprising an actuator for pivoting the implement about the implement axis, the actuator mounted to at least one of: the implement and the platform.

30. The apparatus of claim 25, wherein an orientation of the implement is adjustable relative to the stationary point by moving the arms to selected angular positions about the third axis, without causing significant translation of the active portion of the implement relative to the stationary point.

31. The apparatus of claim 30, wherein a position of the implement is adjustable relative to the stationary point by moving the arms to selected angular positions about the third axis without causing significant translation of the active portion of the implement relative to the stationary point.

32. The apparatus of claim 31, wherein the position and orientation of the active portion of the implement are adjustable over at least a portion of an imaginary spherical surface centered at the stationary point.

33. The apparatus of claim 2, wherein each of the rotary actuators is coupled to the corresponding one of the shafts by a corresponding independently driven gear mechanism.

34. The apparatus of claim 33, wherein the orientation of the platform is adjustable relative to the stationary point by actuating said gear mechanisms to move the arms to selected angular positions about the third axis, without causing significant translation of the stationary point.

35. The apparatus of claim 1, comprising one or more controllers configured to control movement of the arms to the selected angular positions.

36. The apparatus of claim 35, comprising one or more sensors, each sensor connected to sense an angular position of a corresponding one of the arms and to feedback a sensed position to the one or more controllers.

37. The apparatus of claim 2, wherein a length of one or more of the plurality of shafts exceeds a width of the platform.

38. The apparatus of claim 2, wherein a length of each of the plurality of shafts is adjustable along a dimension parallel with the third axis.

39. The apparatus of claim 1, wherein the stationary point is spaced apart from the platform by a distance not exceeding 3 times a width of the platform.

40. The apparatus of claim 1, wherein the stationary point is located within a volume of space occupied by extremities of the platform.

41. A method of orienting and positioning a platform about a stationary point in space, the method comprising:
    (a) providing at least three links, each link having a first end pivotally coupled to the platform about a corresponding first axis;
    (b) providing an arm corresponding to each of the links, each arm pivotally coupled to a second end of the corresponding link about a corresponding second axis; all of the arms pivotable about a common third axis spaced apart from their corresponding second axes; all of the first axes, second axes and third axis extending through the stationary point; and
    (c) pivoting the arms to selected angular positions about the common third axis, to adjust a pose of the platform over an imaginary spherical surface centered at the stationary point, without significantly displacing the stationary point.

42. A method according to claim 41, wherein pivoting the arms to selected angular positions comprises pivoting the links about the first and second axes.

43. A method according to claim 41, wherein pivoting the arms to selected angular positions comprises simultaneously pivoting all of the arms.

44. A method according to claim 41, which comprises fixing an implement to the platform, such that an active portion of the implement is located within operational range of the stationary point.

45. A method according to claim 41, wherein pivoting the arms to selected angular positions comprises adjusting an orientation of the implement relative to the stationary point without causing significant translation of the active portion of the implement relative to the stationary point.

* * * * *